(12) United States Patent
Tsui et al.

(10) Patent No.: US 6,806,725 B2
(45) Date of Patent: Oct. 19, 2004

(54) METHOD AND APPARATUS FOR PROCESSING AN ARRAY OF PACKAGED SEMICONDUCTOR DEVICES

(75) Inventors: Ching Man Stanley Tsui, Kwai Chung (CN); M. Bilan Curito, Jr., Kwai Chung (CN); Lap Kei Eric Chow, Kwai Chung (CN)

(73) Assignee: ASM Assembly Automation, Ltd. (HK)

( * ) Notice: Subject to any disclaimer, the term of this patent is extended or adjusted under 35 U.S.C. 154(b) by 0 days.

(21) Appl. No.: 10/083,177

(22) Filed: Feb. 25, 2002

(65) Prior Publication Data

US 2002/0177875 A1 Nov. 28, 2002

(51) Int. Cl.[7] .......................... G01R 31/02; G01R 31/26
(52) U.S. Cl. .......................... 324/755; 324/754; 438/15
(58) Field of Search ................... 324/754, 755, 324/760, 765, 158.1; 438/14–18, 460, 464

(56) References Cited

U.S. PATENT DOCUMENTS

| | | | | |
|---|---|---|---|---|
| 4,296,542 A | * | 10/1981 | Gotman | 438/17 |
| 4,753,863 A | * | 6/1988 | Spanjer | 430/138 |
| 5,008,615 A | * | 4/1991 | Littlebury | 324/754 |
| 5,389,182 A | * | 2/1995 | Mignardi | 156/344 |
| 5,570,032 A | * | 10/1996 | Atkins et al. | 324/760 |
| 5,634,267 A | * | 6/1997 | Farnworth et al. | 29/840 |
| 5,981,314 A | * | 11/1999 | Glenn et al. | 438/127 |
| 6,064,213 A | * | 5/2000 | Khandros et al. | 324/754 |
| 6,177,288 B1 | * | 1/2001 | Takiar | 438/15 |
| 6,242,933 B1 | * | 6/2001 | Yap | 324/755 |
| 6,287,878 B1 | * | 9/2001 | Maeng et al. | 438/15 |
| 6,392,428 B1 | * | 5/2002 | Kline et al. | 324/755 |
| 6,692,978 B2 | * | 2/2004 | Tandy et al. | 438/26 |

* cited by examiner

*Primary Examiner*—David A. Zarneke
*Assistant Examiner*—Paresh Patel
(74) *Attorney, Agent, or Firm*—Ostrolenk, Faber, Gerb & Soffen, LLP

(57) ABSTRACT

The invention provides a method and apparatus for processing an array of electronic components. It involves providing mounting means to mount unsingulated components onto the mounting means, singulating the components to physically separate them, and testing the singulated electronic components for defects whilst they are mounted on the mounting means, and without removal therefrom.

24 Claims, 4 Drawing Sheets

METHOD AND APPARATUS FOR PROCESSING AN ARRAY OF PACKAGED SEMICONDUCTOR DEVICES

FIELD OF THE INVENTION

This invention relates to a method and apparatus for the handling of arrays of electronic devices, and in particular to the testing and marking of such electronic devices for subsequent processing after they have been electrically separated. The electronic device may be any one of a variety of devices, including but not limited to, a chip on a wafer, a chip scale package (CSP) or chip scale ball grid array (CSBGA) package.

BACKGROUND AND PRIOR ART

The growth of and the demand for miniaturization of consumer electronics (especially portable electronics equipment) has consistently required the reduction of the size of semiconductor packages, while concurrently, die components are becoming denser and pin count of each die is increasing. The drive to achieve increased integrated circuit (IC) capability inside a smaller package has resulted in the development of chip-scale packages (CSP). These new smaller devices are gaining acceptance and the back-end assembly and test infrastructure is consequently coping to meet the challenges of handling and processing these small devices.

Meanwhile, we are seeing the rapid adoption of chip-scale packages such as fine-pitch ball grid array (FBGA) and micro leadframe packages (MLP), which are defined by the package size being no more than 20% larger than the size of the die. The challenges presented by chip-scale packages at the test-stage are primarily in the areas of fixturing and handling.

In a typical semiconductor device manufacturing process called front-end processing, a plurality of integrated circuits is formed on a wafer, such as a silicon wafer. Once the integrated circuits are formed, the wafer is diced into individual chips. The front-end processing of semiconductor devices requires probing to identify the correctly-formed devices and to ink-mark the defective devices. These chips are then packaged for the next assembly line, referred to as back-end processing. Devices inked as defective will be sorted out and only those devices that are correctly-formed will proceed to the next process.

The formation of IC components requires numerous individual process operations, primarily in front-end processing, which are performed in a specific sequence, as known in the art. Each of these operations must be precisely controlled and monitored so that the IC components operate with the required electrical characteristics. However, even though the operations are precisely controlled and monitored, IC component failures still occur. Thus, it is important to detect the defective IC components as early as possible to prevent the unnecessary expense of continuing the fabrication of any defective electronic devices.

The IC components are generally tested after they are fabricated on the wafer and just prior to dicing the wafer into individual chips. These chips are then assembled during back-end processing by electrically connecting the individual pads of the chip to the electrical traces on the substrate for FBGA and at the individual electrical paths on the lead-frame for MLP. The process is known as wire bonding. Typically, 25 μm diameter gold wire is used. The next step in the process is to protect the device from the outside world, by panel-molding the substrate of the electronic device with a laser-markable plastic molding compound, such as that described in U.S. Pat. No. 4,753,863.

The next sequence in the process is to isolate the electronic devices electrically by singulating them into individual electronic devices and then testing them.

Currently, IC chips are often tested and marked individually after singulation. The testing and marking process is difficult and delicate if a typical method of testing the electrical characteristics of the electronic devices after they are formed is used. Such a typical test requires physical contact with the device's individual input and output leads or signal paths. There is a need to reduce processing time and costs by minimizing the individual handling of singulated electronic devices.

The physical contact required for testing generally comprises contacting a plurality of individual balls or pads on an electronic device with a plurality of test contacts housed in the test contactor housing. The test contacts are usually fabricated from metal material and reside in vias that extend into the contactor housing. The test contacts may be biased by a spring mechanism. The test contacts are each in electrical contact with a device interface board within the contactor housing, which directs electrical test signals to the electronic device. The test contacts extend out of the contactor housing vias to contact the electronic device's balls or pads.

The test is not reliable unless the devices are separated electrically. However, to separate them electrically will require them to be separated physically by sawing or other singulation means. The difficulty is to test the electronic devices individually at the testing stage and to identify each individual device as "failed" or "passed" without slowing down the process. Electronic devices on a tape within a wafer ring can be tested for specific electrical characteristics by sending and/or receiving signals through the test contacts. The electronic devices that fail the test procedure are "mapped" such that when an array of devices is diced, the failed electronic devices will not be picked up for packing and can be culled.

Conventional back-end assembly typically comprises many independent processes or if the process is mechanized, it is a process dedicated for particular equipment. Die Bond, Wire Bond, Molding, Ball Placement, Marking, Sawing, and Test and Packing are examples of separate processes and equipment. Conventional back-end assembly and test processing are not favorable for manufacturing small electronic devices. The manufacture of these devices requires full automation processing. Automating and integrating some of the processes and equipment will be beneficial as to profitability and efficiency. Cost reduction is also one of the direct results of automation and integration. Performing functions en masse, rather than one at a time, has always been a method of reducing costs. However, to do so, an innovative system that will provide the means to handle seamless mass manufacturing should be developed. To meet the needs of this new packaging process, an integrated mechanization of singulation, test and marking is required.

SUMMARY OF THE INVENTION

With the foregoing background in mind, it is an object of this invention to provide for test handling electronic devices using a method and an apparatus that can effectively handle an array of electronic devices substantially simultaneously.

It is a further object of the present invention to improve the handling of an array of small electronic devices and increase the productivity of testing, inscribing and collecting electrical devices.

According to one aspect of the invention there is provided a method of processing an array of electronic components comprising the steps of providing mounting means mounting unsingulated electronic components onto the mounting means, singulating the components to physically separate them, and testing the singulated electronic components for defects whilst they are mounted on the mounting means and without removal therefrom.

According to a second aspect of the invention there is provided an apparatus for processing an array of electronic components comprising mounting means for mounting electronic components, a singulating device for singulating the said array of electronic components and a testing device for testing each of the said components for defects, whereby singulation and testing of electronic components are conducted while they are mounted on the mounting means without removal therefrom.

It will be convenient hereinafter to describe the invention in greater detail by reference to the accompanying drawings which illustrate one embodiment of the invention. The particularity of the drawings and the related description is not to be understood as superseding the generality of the broad identification of the invention as defined by the claims.

DETAILED DESCRIPTION OF THE PREFERRED EMBODIMENTS OF THE INVENTION

Figure 1A:
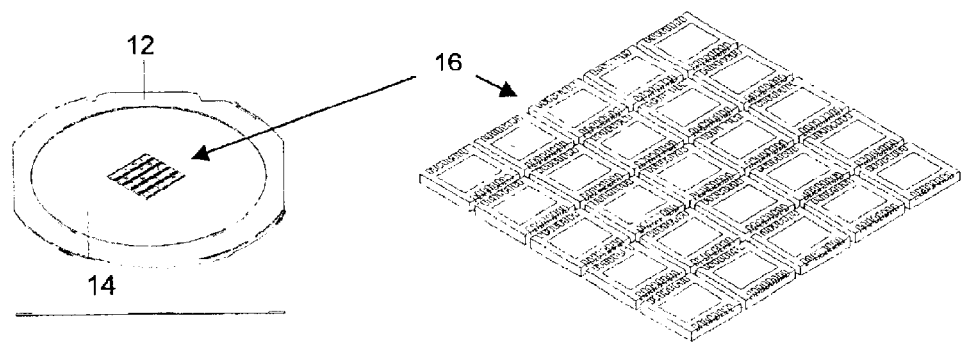
FIGS. 1(a) to (c) are respectively illustrations of arrangements of electronic devices on a singulation tape secured by a singulation frame, and an arrangement of a singulation saw with respect to the electronic devices.

FIG. 1(a) shows a mounting means in the form of a support or singulation frame 12, to which a film of singulation film or tape 14 with an adhesive compound on one side of the tape 14 is secured, being stiffened by the frame 12. Tapes 14 suitable for this purpose preferably consist of a transparent film with adhesive on one side of the film that allows electronic devices to stick to the surface thereof, thereby to be secured to the tape. A cassette on-loader (not shown) accepts unsingulated electronic devices 16 in the form of strips, the dies of the electronic devices 16 having been covered by plastic or encapsulation. A substrate containing electronic devices is mounted onto the tape 14, stiffened by the singulation frame 12 which comprises a circular ring that may be made of stainless steel. The frame 12 stiffens the tape 14 by ensuring that the tape 14 is taut. A micro-porous air-permeable aluminium plate (such as a Portec METAPOR® F100 AL plate) may be used on the surface of a vacuum chuck 21, 22 to provide suction flow on its surface.

Figure 1B:
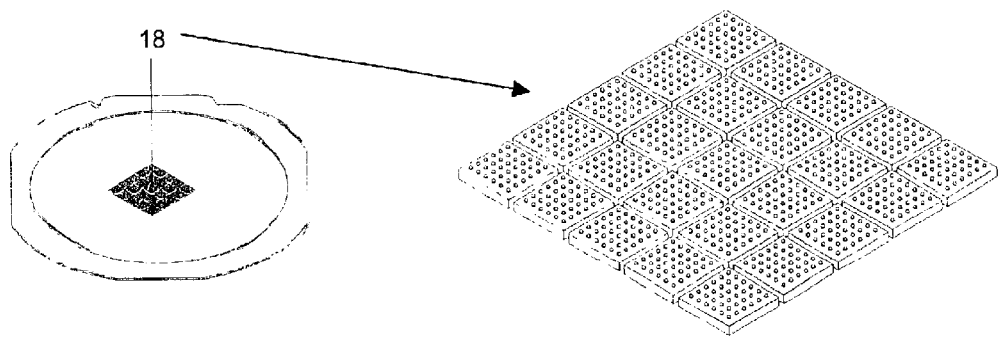

On the adhesive side of the singulation tape 14, there is arranged an array of CSP packages 16 that are to be singulated. The electrical contacts of the CSP packages 16 face away from the tape 14 to allow the contacts to be tested. To the right of FIG. 1(a), an enlarged view of an array of CSP packages that have been singulated is illustrated. FIG. 1(b) shows the singulation frame 12 and adhesive singulation tape 14 with CSBGA packages 18 thereon, wherein the electrical contacts of the CSBGA packages 18 face away from the tape 14. To the right of FIG. 1(b), there is an enlarged view of CSBGA packages 18 that have been singulated. These exemplary CSP packages and CSBGA packages will hereinafter be referred to collectively as "electronic devices 16".

Figure 1C:
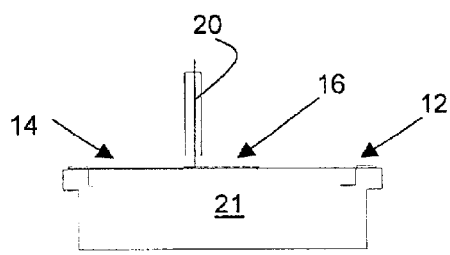

FIG. 1(c) is a side elevation view of a singulation frame 12 placed onto a vacuum chuck 21 to secure it in position during the singulation process by a singulation device. Electronic devices 16 are arranged on the singulation tape 14, and a singulation saw 20 is positioned along cutting lines of the plurality of electronic devices 16 to dice the devices 16 and separate them physically.

Figure 2:
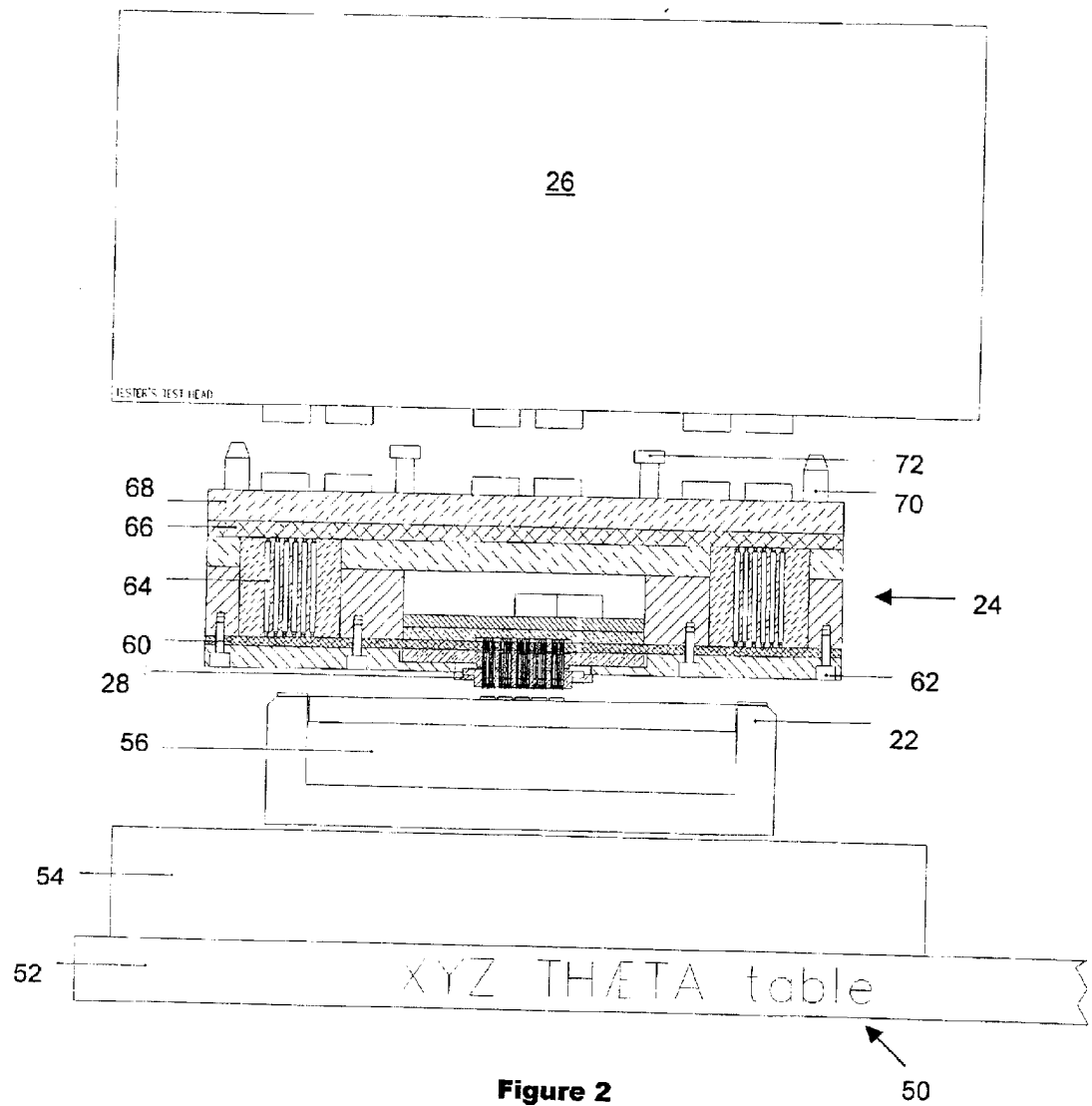
FIG. 2 is a cross-sectional view of a testing position of an apparatus according to a preferred embodiment of the invention, including a tester's test head, a test contactor and schematic illustrations of some of its component parts, including a vacuum chuck and an XYZ-Theta table.

FIG. 2 is a cross-sectional view of a testing position of an apparatus 10 according to a preferred embodiment of the invention, showing a testing device comprising a tester's test head 26, a test contactor 24 and schematic illustrations of some of its component parts, a vacuum chuck 22 and means, such as an XYZ-Theta ("XYZ-θ") table 50, that can move the vacuum chuck in linear and rotary axes. The XYZ-θ table is used to move and locate the singulated devices 16 to the locations where testing, inverting and inscribing of the devices 16 are performed. The test contactor 24 comprises a plurality of contact pins 28 with a receptacle therefor, a contact board 60 behind the contact pins 28 and electrically connected therewith, and double-ended contact pins 64 electrically connecting the contact board 60 to a device interface board 66. Alignment pins 62 with locking mechanisms are used to align the contact pins 28. A device interface board stiffener 68 completes the test contactor housing. There are also test head alignment pins 70 and test head locking mechanisms 72 to align and engage the test contactor 24 to the tester's test head 26. The XYZ-Theta table 50 includes an x-axis mount 52, y-axis mount 54 and theta mount 56 which allow the electronic devices to be oriented in the x, y, z and rotary axes.

Figure 3:
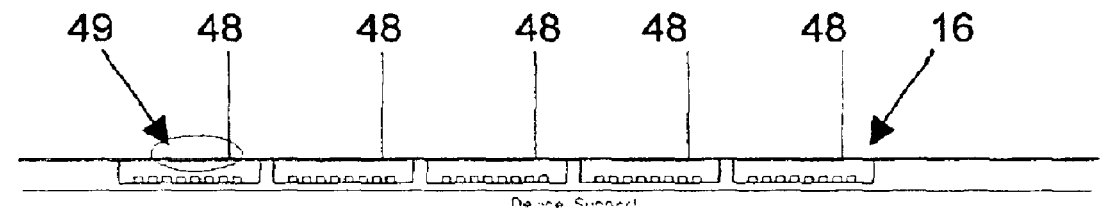
FIG. 3 shows cross-sectional views of the electronic devices secured to the singulation tape in inverted positions at an inscribing position of the apparatus, and a laser beam for inscribing a surface of the electronic devices that is attached to the singulation tape.
Figure 3:
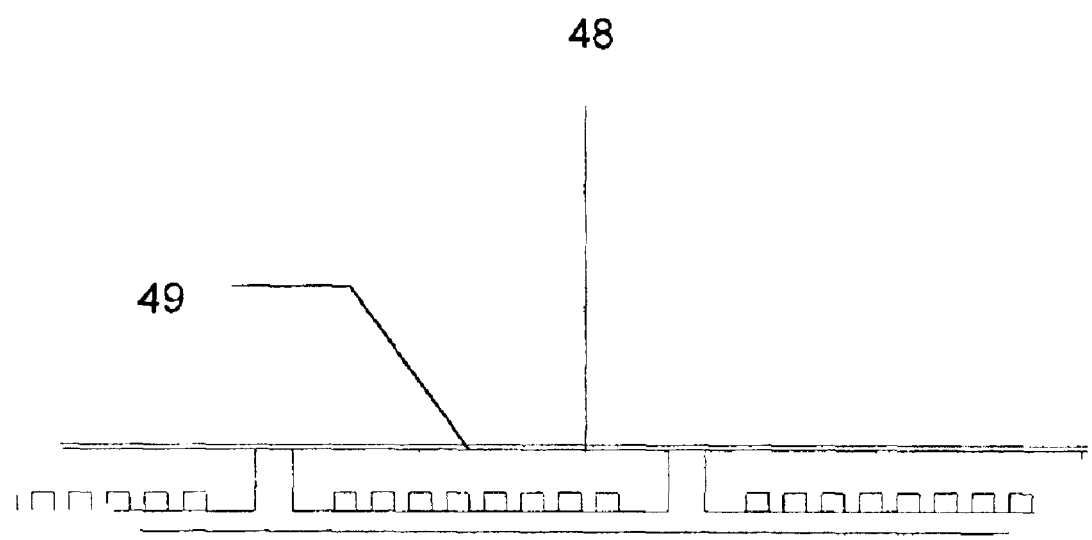

FIG. 3 shows cross-sectional views of the electronic devices 16 secured to the singulation tape 14 by the adhesive in an inverted position at an inscribing position of the apparatus, wherein the electronic devices 16 are resting on the vacuum chuck 22. An inscribing device such as a laser beam 48 is irradiated to inscribe markings 49 on a surface of the electronic devices 16 that is attached to the adhesive side of the singulation tape 14, through the singulation tape 14. Thus, the singulation tape 14 should be substantially transparent to the laser beam so as not to absorb the laser energy. Moulding compound used for the electronic device 16 should thus be one that is laser-markable, such as that described in U.S. Pat. No. 4,753,863.

Alternatively, instead of marking the surface of the electronic device 16 opposite the electrical contacts, marking of the devices 16 on the same side as the contacts could conceivably by envisaged, in which event, there would be no need to invert the singulation frame 12 before marking using this particular embodiment of the invention.

Figure 4:
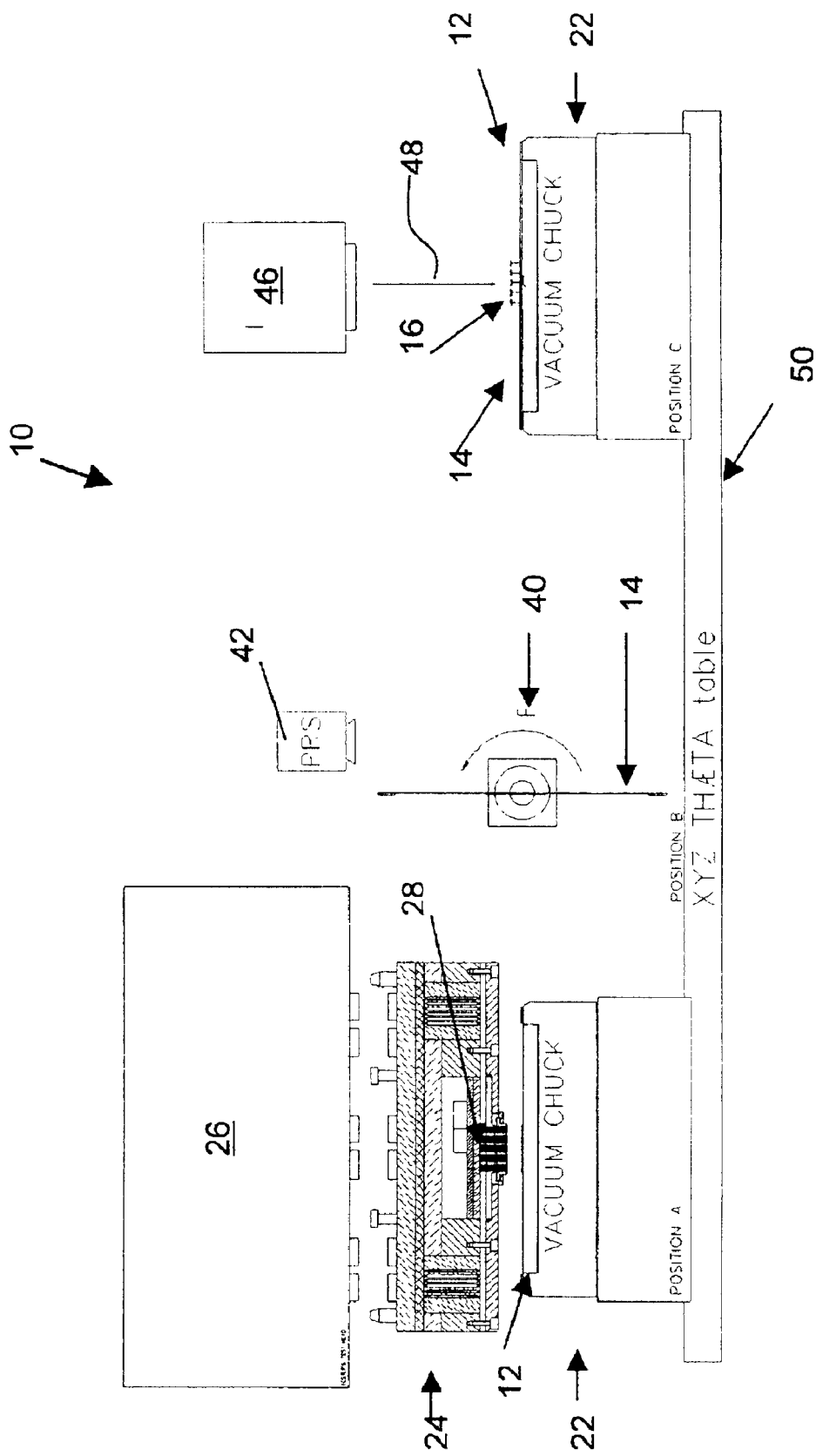
FIG. 4 is a schematic illustration of an apparatus according to the invention, showing testing, inverting and inscribing positions respectively of the apparatus.

FIG. 4 is a schematic representation of a test-handling apparatus 10 according to the preferred embodiment of the invention, including a testing position (position A), flipping or rotating position (position B) and inscribing position (position C).

The present invention may include a loader (not shown) of singulation frames 12 having electronic devices 16 after the devices are singulated by a dicing saw 20. The electronic devices 16 are loaded by the loader onto the vacuum chuck 22 of the XYZ-θ table at position B. An orientating device, preferably an image recognition vision system (eg. Pattern Recognition System or "PRS") 42 could be used as a means of checking the location and correct positions of the devices. After the location and position of each device has been verified by the PRS 42, the XYZ-θ table 50 will move the array of electronic devices 16 to testing position A just below the test contactor 24 to be tested. An image stored in the PRS 42 will guide the system for positional accuracy, and with reference to such an image, the XYZ-θ table 50 will align the array of electronic devices 16 according to the orientation of the test contactor 24 for testing.

The tester's test head 26 is engaged to the test contactor 24 to provide electrical contact between the two devices. Once the electronic devices 16 are correctly orientated, the vacuum chuck 22 will be raised so that the contact pins 28 are in electrical contact with the electronic devices 16. The array of electronic devices 16 will then be mapped so that the positions of any defective devices 16 can be located, in relation to the image of the array that had been obtained previously. This is to facilitate the removal of defective devices 16 later on in the process.

It is preferred that when testing the array of electronic devices 16, the pattern of contacting the contact pins 28 with each device-under-test is such that adjacent devices 16 are not tested simultaneously. This is to isolate an electronic device 16 under test from adjacent devices 16 to minimize cross-talk, interference and/or distortions, especially when testing Radio Frequency (RF). For example, if one device 16 is to be tested at a time, contact pins 28 may repeatedly move in sequence through the odd rows of the array, and then return to repeatedly move through the even rows of the array. The process is repeated until all the rows and columns of the array are tested. In the case where there are a plurality of contact pins 28 testing a plurality of test sites, a number of electronic devices 16 can be tested with each raising of the electronic devices 16 to contact the contact pins 28, but in any event, it is preferable that no two adjacent devices 16 are tested at the same time.

After the positions of any defective devices 16 are mapped, the vacuum chuck 22 together with the singulation frame 12, singulation tape 14 and electronic devices 16, are moved by the XYZ-θ table 50 to an inverting device, which in this embodiment is a flip mechanism 40, at position B. The flip mechanism 40 inverts the singulation frame 12 so that the electronic devices 16 are now positioned on the bottom of the singulation tape 14, with the adhesive side of the singulation tape 14 facing downwards. This will subject the surface of the devices 16 opposite to the surface on which electrical contacts are located (usually used as a marking surface) to be accessible by a laser beam 48 for irradiation. Since the singulation tape 14 has adhesive properties, the electronic devices 16 are secured to the tape 14 notwithstanding the inversion of the singulation frame 12.

The XYZ-θ table 50 will then move the vacuum chuck 22, singulation frame 12 and electronic devices 16 just below the laser marker 46 at the inscribing position (C). A primary function of the laser head 46 is to mark the electronic devices 16 that passed the test, for identification. The devices will be marked according to the test map or the results that are transmitted by the test system. The laser beam 48 (which is created by light amplification from the stimulated emission of radiation) will be adjusted according to the appropriate intensity of the beam to inscribe onto the surfaces of the devices 16. The beam of light will pass through the transparent singulation tape 14 without any damage to the tape 14 whereas the opaque surfaces of the electronic devices 16 will be marked by being scorched. All this time, the electrical devices 16 remain attached to the singulation tape 14.

After laser-marking at position C, the vacuum chuck 22 is shifted back to position B. The PRS 42 is then employed to determine and locate each of the electronic devices 16 that have been marked as faulty. Thereafter, the singulation frame 12 will be moved to off-load the non-faulty devices 16 into a magazine for the next process. The electronic devices 16 may then be removed by a pick-and-place device (not shown) or other off-loading means and may be stored inside a cassette or a magazine.

The electronic device 12 may be a simple logic device or a simple memory device or a mixed signal device or memory device with exposed input and output signal paths. Further the system and method may involve testing more than one device at a time. The testing handling apparatus 10 may also include a singulation saw 20 to singulate the array of electronic devices 16 on the singulation frame 12. The present invention may further include an on-loader to load the singulated devices 16 onto the XYZ-θ table 50 or manually load the singulated devices onto the XYZ-θ table 50.

The invention described herein is susceptible to variations, modifications and/or additions other than those specifically described and it is to be understood that the invention includes all such variations, modifications and/or additions which fall within the spirit and scope of the above description.

What is claimed is:

1. A method of processing an unsingulated array of packaged semiconductor devices comprising the steps of:
    mounting the singulated array of packaged semiconductor devices on a mounting device; then singulating the packaged semiconductor devices to physically separate the packages; and then
    testing the singulated packaged semiconductor devices for defects while they are mounted on the mounting device and without removal therefrom.

2. A method according to claim 1, further comprising the step of applying markings to distinguish non-defective ones of the packaged semiconductor devices from defective ones after testing while they are still mounted on the mounting device.

3. A method according to claim 2, wherein the singulation, testing and marking steps are carried out at two or more stations.

4. A method according to claim 3, including the step of moving the packaged semiconductor devices at least between the testing and marking positions for testing and marking respectively.

5. A method according to claim 1, further including the step of detecting the alignments of the packaged semiconductor devices before testing, and orienting the array of packaged devices as desired before testing.

6. A method according to claim 2, wherein the markings are applied by directing a laser beam onto selected ones of the packages.

7. A method according to claim 6, wherein:
the mounting device comprises a film of laser transparent tape with an adhesive on one surface;
wherein the packaged semiconductor devices are mounted on the adhesive surface of the film of transparent tape; and
marking is effected by passing the laser beam through the film of laser transparent tape toward the adhesive surface thereof,
the surface of the packaged semiconductor device being marked being the one in contact with the adhesive surface of the tape.

8. A method according to claim 1, wherein the packaged semiconductor devices are maintained in a substantially coplanar relationship on the mounting device during testing.

9. A method according to claim 1, wherein the packaged semiconductor devices are tested in subsets selected such that adjacent devices are not tested simultaneously.

10. An apparatus for processing an unsingulated array of packaged semiconductor devices comprising:
a mounting device for mounting the unsingulated array of packaged semiconductor devices;
a singulating device for singulating the array of packaged semiconductor devices; and
a testing device operative to test each of the singulated packaged semiconductor devices for defects;
whereby singulation and testing of the singulated packaged semiconductor devices are conducted while they are mounted on the mounting device without removal therefrom.

11. An apparatus according to claim 10, including an inscribing device for applying markings to distinguish defective and non-defective tested packaged semiconductor devices while they are mounted on the mounting device.

12. An apparatus according to claim 11, wherein the singulation, testing and marking are carried out at two or more stations of the apparatus.

13. An apparatus according to claim 12, including a conveyor for moving the packaged semiconductor devices for processing at least between the testing and marking positions.

14. An apparatus according to claim 13, wherein the conveyor is adapted to move the packaged semiconductor devices relative to linear and rotary axes.

15. An apparatus according to claim 10, wherein the mounting means device comprises a film of material stretched on a support frame, and having an adhesive on one side for receiving the packaged semiconductor devices.

16. An apparatus according to claim 15, further including a vacuum chuck operative to maintain the position of the support frame and film during the singulation, testing and marking of the packaged semiconductor devices.

17. An apparatus according to claim 10, including an orienting device to adjust alignment of the packaged semiconductor devices and/or to locate the positions of defective ones of the packaged semiconductor devices.

18. An apparatus according to claim 17, wherein the orienting device is an image recognition vision system.

19. An apparatus according to claim 11, wherein the inscribing device is a laser device operative to mark a surface of the packaged semiconductor device by heating the surface.

20. An apparatus according to claim 19, wherein:
the mounting device comprises a film of transparent tape with an adhesive surface on which the packaged semiconductor devices are mountable; and
the laser device is operative to direct the laser beam generated thereby through the film toward the adhesive surface thereof to mark packaged semiconductor devices mounted on the adhesive surface.

21. An apparatus according to claim 20, including an inverting device to invert the transparent tape to expose the surface of each packaged semiconductor device mounted on said adhesive surface of the transparent tape to the laser device for marking.

22. An apparatus according to claim 14, wherein the conveyor is an XYZ-Theta table.

23. An apparatus according to claim 10, wherein the packaged semiconductor devices are maintained in a substantially coplanar relationship on the mounting device during testing.

24. An apparatus according to claim 10, wherein the packaged semiconductor devices are tested in subsets selected such that adjacent devices are not tested simultaneously.

* * * * *

UNITED STATES PATENT AND TRADEMARK OFFICE
CERTIFICATE OF CORRECTION

PATENT NO. : 6,806,725 B2
DATED : October 19, 2004
INVENTOR(S) : Ching Man Stanley Tsui, M. Bilan Curito, Jr. and Lap Kei Eric Chow It is certified that error appears in the above-identified patent and that said Letters Patent is hereby corrected as shown below:

Column 6,
Line 45, change "singulated" to -- unsingulated --.

Signed and Sealed this

Twelfth Day of July, 2005

JON W. DUDAS
*Director of the United States Patent and Trademark Office*